US011207681B2

(12) United States Patent
Chung et al.

(10) Patent No.: US 11,207,681 B2
(45) Date of Patent: Dec. 28, 2021

(54) METHOD FOR EXTRACTING NUCLEIC ACID AND EXTRACTION CASSETTE THEREOF

(71) Applicant: Delta Electronics, Inc., Taoyuan (TW)

(72) Inventors: Wei-Yu Chung, Taoyuan (TW); Song-Bin Huang, Taoyuan (TW); Shing-Lun Liu, Taoyuan (TW); Yu-Kai Kao, Taoyuan (TW); Yi-Chen Li, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 447 days.

(21) Appl. No.: 16/229,685

(22) Filed: Dec. 21, 2018

(65) Prior Publication Data

US 2019/0118180 A1 Apr. 25, 2019

Related U.S. Application Data

(63) Continuation-in-part of application No. 15/018,067, filed on Feb. 8, 2016, now Pat. No. 10,213,783.

(Continued)

(30) Foreign Application Priority Data

Jul. 17, 2015 (TW) .................................. 104123190
Dec. 14, 2018 (CN) .......................... 201811535018.6

(51) Int. Cl.
*B01L 3/00* (2006.01)
*C12N 15/10* (2006.01)
*B01L 7/00* (2006.01)

(52) U.S. Cl.
CPC ....... *B01L 3/502738* (2013.01); *B01L 3/5027* (2013.01); *B01L 7/52* (2013.01);
(Continued)

(58) Field of Classification Search
CPC .... B01L 3/502738; B01L 3/5027; B01L 7/52; B01L 2300/069; B01L 2300/0681;
(Continued)

(56) References Cited

U.S. PATENT DOCUMENTS 7,192,559 B2 3/2007 Chow et al.
2005/0045538 A1 3/2005 Seto et al.
(Continued)

FOREIGN PATENT DOCUMENTS

CN 101765463 A 6/2010
GB 2516666 A 2/2015
(Continued)

OTHER PUBLICATIONS

Extended Search Report of corresponding EP Application No. 18215536.6 dated Apr. 10, 2019, 8 pages.

*Primary Examiner* — Matthew D Krcha
*Assistant Examiner* — Jacqueline Brazin
(74) *Attorney, Agent, or Firm* — Muncy, Geissler, Olds & Lowe, P.C.

(57) ABSTRACT

The present invention provides an extraction cassette, which includes an extraction module. The extraction module includes an extraction module body, an expansion compartment, a reaction compartment, a filter, a collection compartment, a first waste-liquid compartment and a second waste-liquid compartment. The expansion compartment is formed on the extraction module body. The reaction compartment includes a reaction compartment inlet, a reaction compartment outlet and a reaction compartment notch, the expansion compartment is connected to the reaction compartment notch, and the reaction compartment notch is located between the reaction compartment inlet and the reaction compartment outlet. The filter is disposed in the reaction compartment and corresponding to the reaction compart- (Continued)

ment outlet. The collection compartment communicates with the reaction compartment outlet. The first waste-liquid compartment communicates with the reaction compartment outlet. The second waste-liquid compartment communicates with the reaction compartment outlet.

12 Claims, 15 Drawing Sheets

Related U.S. Application Data

(60) Provisional application No. 62/610,444, filed on Dec. 26, 2017.

(52) U.S. Cl.
CPC .... *C12N 15/1003* (2013.01); *B01L 2200/028* (2013.01); *B01L 2200/0684* (2013.01); *B01L 2300/047* (2013.01); *B01L 2300/06* (2013.01); *B01L 2300/069* (2013.01); *B01L 2300/0681* (2013.01); *B01L 2300/0877* (2013.01); *B01L 2300/14* (2013.01); *B01L 2400/0487* (2013.01)

(58) Field of Classification Search
CPC ..... B01L 2200/0684; B01L 2400/0487; B01L 2200/028; B01L 2300/14; B01L 2300/06; B01L 2300/0877; B01L 2300/047; C12N 15/1003

USPC ........................................................ 436/178
See application file for complete search history.

(56) References Cited

U.S. PATENT DOCUMENTS

| | | |
|---|---|---|
| 2005/0142571 A1 | 6/2005 | Parthasarathy et al. |
| 2006/0019379 A1* | 1/2006 | Taylor .................... C12M 47/06 435/306.1 |
| 2006/0110725 A1 | 5/2006 | Lee et al. |
| 2006/0172642 A1 | 8/2006 | Sasaki et al. |
| 2008/0121591 A1 | 5/2008 | Knight et al. |
| 2009/0148933 A1 | 6/2009 | Battrell et al. |
| 2010/0216225 A1 | 8/2010 | Dyer et al. |
| 2014/0206073 A1 | 7/2014 | Park et al. |
| 2016/0130640 A1* | 5/2016 | Wright ................ B01F 7/00141 506/39 |

FOREIGN PATENT DOCUMENTS

| | | |
|---|---|---|
| TW | 201326814 A1 | 7/2013 |
| WO | WO 2005/073691 A1 | 8/2005 |
| WO | WO 2005/111210 A1 | 11/2005 |
| WO | WO 2006/032044 A2 | 3/2006 |
| WO | WO 2007/149791 A2 | 12/2007 |
| WO | WO 2008/149111 A1 | 12/2008 |
| WO | WO 2010/091080 A2 | 8/2010 |

\* cited by examiner

METHOD FOR EXTRACTING NUCLEIC ACID AND EXTRACTION CASSETTE THEREOF

CROSS REFERENCE TO RELATED APPLICATIONS

This application claims the benefit of U.S. Provisional Application No. 62/610,444, filed Dec. 26, 2017 the entirety of which is incorporated by reference herein.

This application is a Continuation-In-Part of pending U.S. patent application Ser. No. 15/018,067, filed Feb. 8, 2016 and entitled "Nucleic acid extracting device".

This Application claims priority of China Patent Application No. 2018115350186, filed on Dec. 14, 2018, the entirety of which is incorporated by reference herein.

BACKGROUND OF THE INVENTION

Field of the Invention

The present invention relates to an extraction cassette, and in particular to an extraction cassette with an extraction module.

Description of the Related Art

The conventional extraction module is only for extracting nucleic acid, which cannot receive waste-liquid. Since the waste-liquid may pollute the filter inside the reaction compartment, the conventional waste-liquid compartment is far away from the collection compartment. The waste-liquid compartment and the reaction compartment are disposed on different modules, and the size and cost of the conventional extraction cassette are increased.

Conventionally, an all-in-one extraction module is provided, which extracts nucleic acid by the magnetic bead extraction technology. However, the efficiency and purity of the magnetic bead extraction technology are unqualified.

BRIEF SUMMARY OF THE INVENTION

In one embodiment, an extraction cassette is provided. The extraction cassette includes a liquid receiving module and an extraction module. The extraction module communicates with the liquid receiving module. The extraction module includes an extraction module body, an expansion compartment, a reaction compartment, a filter, a collection compartment, a first waste-liquid compartment and a second waste-liquid compartment. The expansion compartment is formed on the extraction module body. The reaction compartment is formed on the extraction module body, wherein the reaction compartment includes a reaction compartment inlet, a reaction compartment outlet and a reaction compartment notch, the expansion compartment is connected to the reaction compartment notch, and the reaction compartment notch is located between the reaction compartment inlet and the reaction compartment outlet. The filter is disposed in the reaction compartment and corresponding to the reaction compartment outlet. The collection compartment is formed on the extraction module body and communicates with the reaction compartment outlet. The first waste-liquid compartment is formed on the extraction module body, wherein the first waste-liquid compartment communicates with the reaction compartment outlet. The second waste-liquid compartment is formed on the extraction module body, wherein the second waste-liquid compartment communicates with the reaction compartment outlet.

In one embodiment, the reaction compartment includes a cone-shaped portion, the filter is disposed on the cone-shaped portion, and the reaction compartment outlet is formed on one end of the cone-shaped portion.

In one embodiment, the extraction module further includes a first path and a second path, the first path connects the reaction compartment outlet to the first waste-liquid compartment and the second waste-liquid compartment, and the second path connects the reaction compartment outlet to the collection compartment.

In one embodiment, the first path intersects the second path at the reaction compartment outlet, a stopper wall is formed in the second path, and the stopper wall is formed on one end of the second path and is adjacent to the reaction compartment outlet.

In one embodiment, the extraction module further includes a third path and a fourth path, the third path connects the first path to the first waste-liquid compartment, and the fourth path connects the first path to the second waste-liquid compartment.

In one embodiment, the first waste-liquid compartment includes a first waste-liquid compartment connection hole, the second waste-liquid compartment includes a second waste-liquid compartment connection hole, the third path connects the first path to the first waste-liquid compartment connection hole, the fourth path connects the first path to the second waste-liquid compartment connection hole, and at least one portion of the second waste-liquid compartment is located between the first waste-liquid compartment connection hole and the second waste-liquid compartment connection hole.

In one embodiment, at least one portion of the fourth path extends in a first direction, and the first direction is away from the first waste-liquid compartment.

In one embodiment, the second waste-liquid compartment includes a second waste-liquid compartment pressure hole, and at least one portion of the waste-liquid compartment is located between the first waste-liquid compartment and the second waste-liquid compartment pressure hole.

In one embodiment, at least one portion of the second path extends in the first direction.

In one embodiment, the collection compartment includes a collection compartment pressure hole, and at least one portion of the collection compartment is located between the first waste-liquid compartment and the collection compartment pressure hole.

In one embodiment, the extraction module further includes an absorbing material, the absorbing material is disposed in the first waste-liquid compartment, the first waste-liquid compartment includes a first waste-liquid compartment pressure hole, and at least one portion of the absorbing material is located in a space of the first waste-liquid compartment between the first waste-liquid compartment pressure hole and the first waste-liquid compartment connection hole.

In one embodiment, the first waste-liquid compartment pressure hole, the second waste-liquid compartment pressure hole and the collection compartment pressure hole are on the same plane.

In one embodiment, the expansion compartment further includes an expansion compartment inlet, an expansion compartment pressure hole and an expansion compartment spacer, the expansion compartment spacer is located between the expansion compartment inlet and the expansion compartment pressure hole, and the expansion compartment spacer is bent toward the expansion compartment pressure hole.

In one embodiment, a method for extracting nucleic acid is provided. The method for extracting nucleic acid includes the following steps. First, an extraction cassette is provided, wherein the extraction cassette includes a liquid receiving module and an extraction module, the extraction module communicates with the liquid receiving module, the extraction module includes a reaction compartment, a filter, a collection compartment, a first waste-liquid compartment and a second waste-liquid compartment. Next, a mixed liquid of sample and alcohol is moved from the liquid receiving module to the extraction module, and the filter captures nucleic acid from the mixed liquid. Then, the mixed liquid is moved to the first waste-liquid compartment. Next, a first detergent is moved from the liquid receiving module to the extraction module, wherein the first detergent passes through the reaction compartment and the filter. Then, the first detergent is moved to the first waste-liquid compartment.

In one embodiment, the method for extracting nucleic acid further includes the following steps. First, a second detergent is moved from the liquid receiving module to the extraction module, wherein the second detergent passes through the reaction compartment and the filter. Then, the second detergent is moved to the second waste-liquid compartment. Next, an eluent is moved from the liquid receiving module to the extraction module, wherein the eluent is resting in the reaction compartment. Then, a positive pressure is provided via a second waste-liquid compartment pressure hole of the second waste-liquid compartment, and a negative pressure is provided via a collection compartment pressure hole of the collection compartment, wherein the eluent with the nucleic acid is moved to the collection compartment.

Utilizing the extraction module of the embodiment of the present invention, the reaction compartment and the waste-liquid compartments are incorporated in one single extraction module, and the size and cost of the extraction cassette are reduced. Particularly, by the design of the paths, the reaction compartment, the collection compartment, the first waste-liquid compartment and the second waste-liquid compartment and by the pressure supply, the waste-liquid can be controlled to be moved to the first waste-liquid compartment and the second waste-liquid compartment, and the eluent with the nucleic acid is controlled to be moved to the collection compartment. The waste-liquid is prevented from polluting the reaction compartment and the collection compartment.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the present invention. This description is made for the purpose of illustrating the general principles of the present invention and should not be taken in a limiting sense. The scope of the present invention is best determined by reference to the appended claims.

Figure 1A:
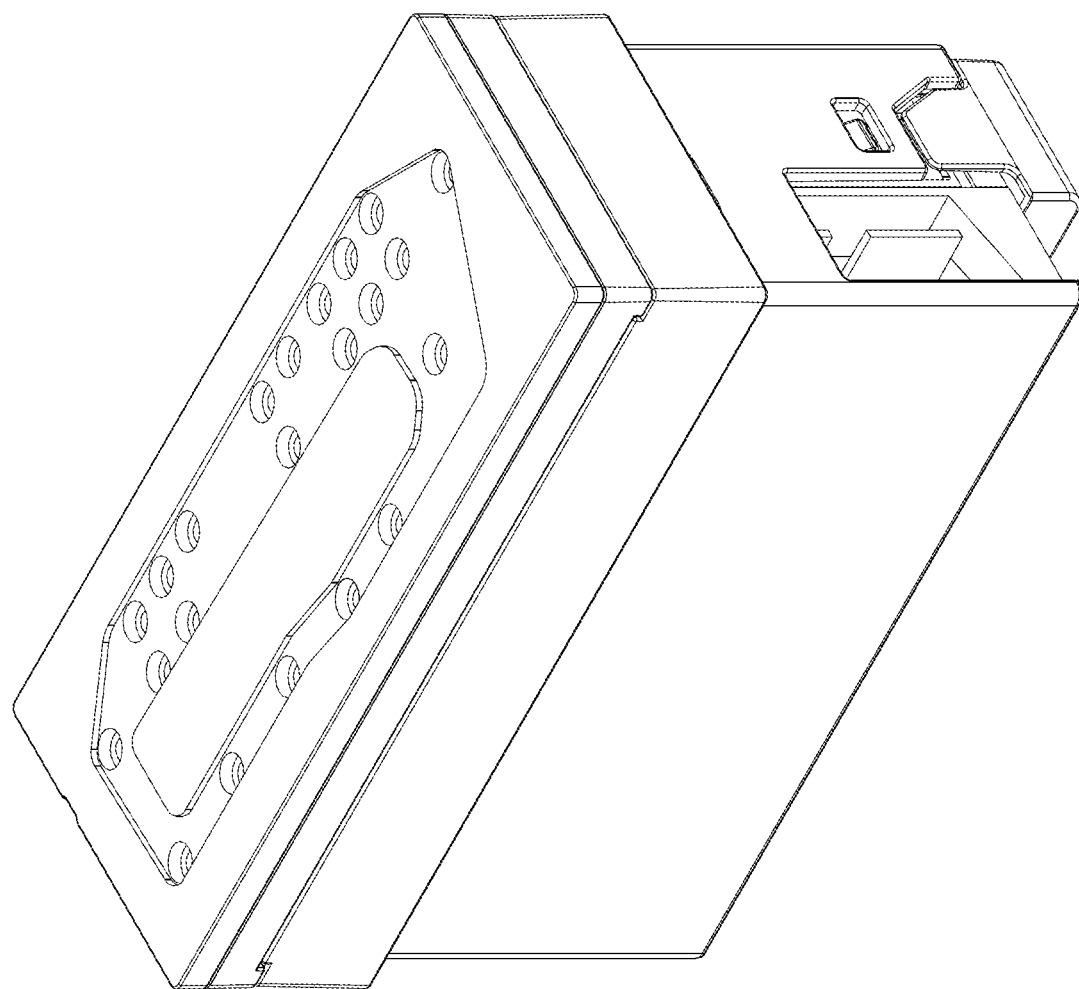
FIG. 1A is an assembled view of an extraction cassette of an embodiment of the present invention.
Figure 1B:
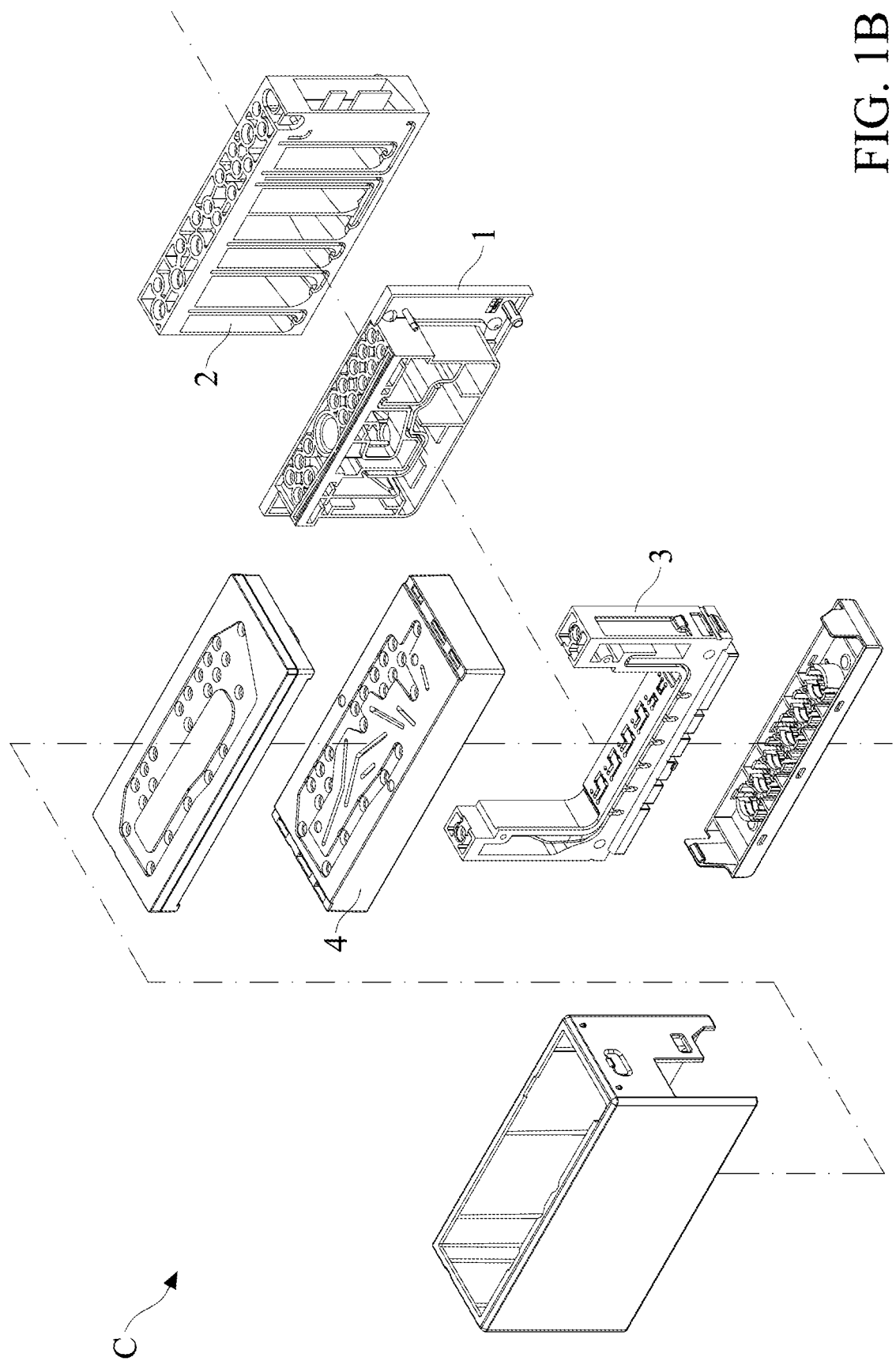
FIG. 1B is an exploded view of the extraction cassette of the embodiment of the present invention.

FIG. 1A is an assembled view of an extraction cassette C of an embodiment of the present invention. FIG. 1B is an exploded view of the extraction cassette C of the embodiment of the present invention. With reference to FIGS. 1A and 1B, the extraction cassette C includes an extraction module 1, a liquid receiving module 2, a sampling module 3 and a connection module 4. The extraction cassette C is adapted to be disposed into an analyzer. The analyzer includes a first pressure supplying module, an analyzing module and a second pressure supplying module. The first pressure supplying module and the second pressure supplying module provide pressure toward the extraction cassette C to control the liquid movement inside the extraction cassette C. The analyzing module heats and cools the extraction cassette C, and analyzes the sample inside extraction cassette C.

Figure 2:
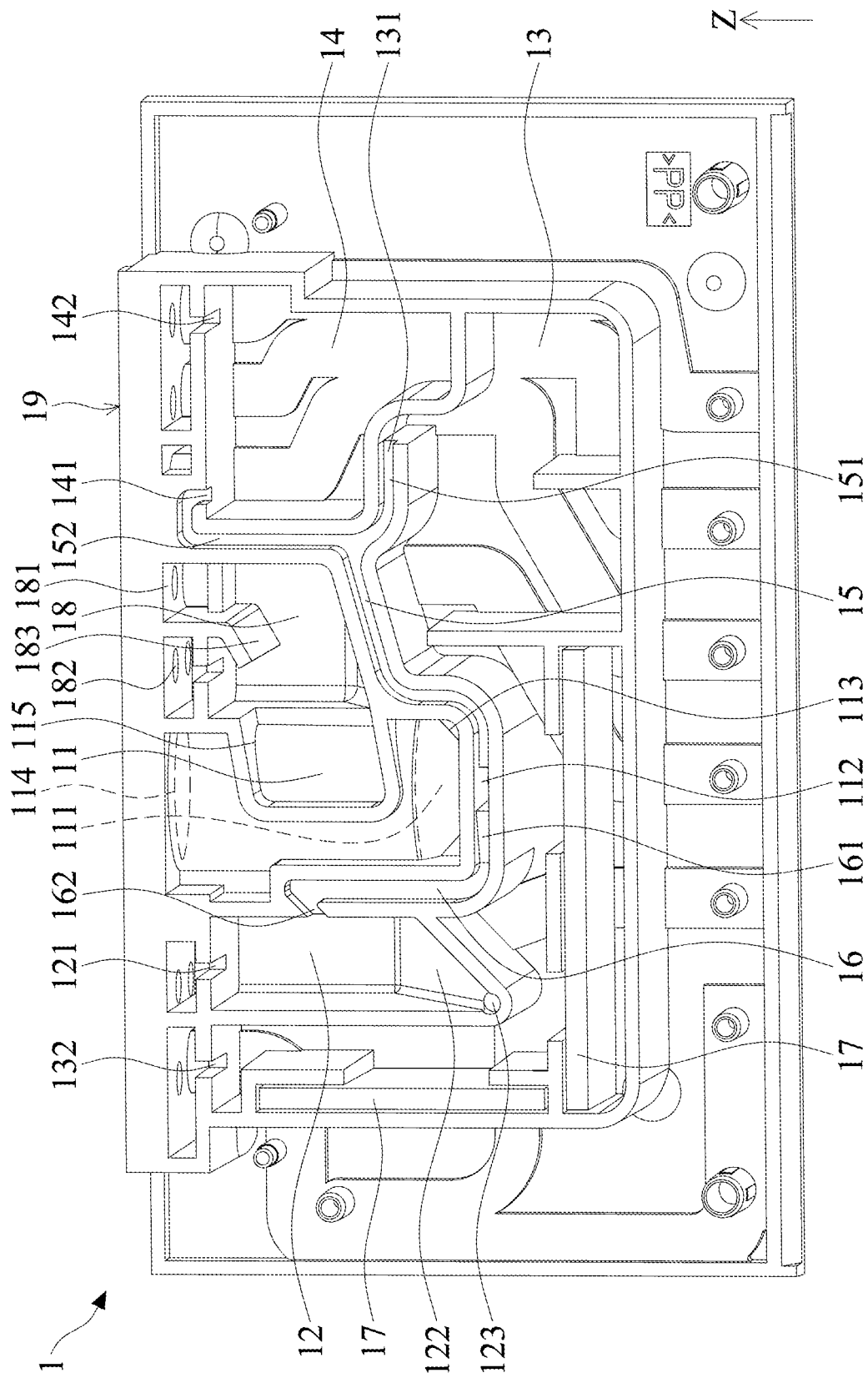
FIG. 2 shows the details of the extraction module of the embodiment of the present invention.

With reference to FIG. 1B, the liquid receiving module 2 communicates with the extraction module 1 via the connection module 4. FIG. 2 shows the details of the extraction module 1. With reference to FIG. 2, the extraction module 1 includes an extraction module body 19, an expansion compartment 18, a reaction compartment 11, a filter 111, a collection compartment 12, a first waste-liquid compartment 13 and a second waste-liquid compartment 14. The expansion compartment 18 is formed on the extraction module body 19. The reaction compartment 11 is formed on the extraction module body 19. The reaction compartment 11 includes a reaction compartment inlet 114, a reaction compartment outlet 112 and a reaction compartment notch 115. The expansion compartment 18 is connected to the reaction compartment notch 115. The reaction compartment notch 115 is located between the reaction compartment inlet 114 and the reaction compartment outlet 112. The filter 111 is disposed in the reaction compartment 11 and corresponding to the reaction compartment outlet 112. The collection compartment 12 is formed on the extraction module body 19 and communicates with the reaction compartment outlet 112. The first waste-liquid compartment 13 is formed on the extraction module body 19. The first waste-liquid compartment 13 communicates with the reaction compartment outlet 112. The second waste-liquid compartment 14 is formed on the extraction module body 19, wherein the second waste-liquid compartment 14 communicates with the reaction compartment outlet 112.

With reference to FIG. 2, in one embodiment, the expansion compartment 18 further includes an expansion compartment inlet 181, an expansion compartment pressure hole 182 and an expansion compartment spacer 183. The expansion compartment spacer 183 is located between the expansion compartment inlet 181 and the expansion compartment pressure hole 182. The expansion compartment spacer 183 is bent toward the expansion compartment pressure hole 182. The expansion compartment spacer 183 prevents the liquid entering the expansion compartment 18 via the expansion compartment inlet 181 from polluting the expansion compartment pressure hole 182.

With reference to FIG. 2, in one embodiment, the reaction compartment 11 includes a cone-shaped portion 113. The filter 111 is disposed on the cone-shaped portion 113. The reaction compartment outlet 112 is formed on one end of the cone-shaped portion 113. In one embodiment, the extraction module 1 further includes a first path 15 and a second path 16. The first path 15 connects the reaction compartment outlet 112 to the first waste-liquid compartment 13 and the second waste-liquid compartment 14. The second path 16 connects the reaction compartment outlet 112 to the collection compartment 12.

With reference to FIG. 2, in one embodiment, the first path 15 intersects the second path 16 at the reaction compartment outlet 112. A stopper wall 161 is formed in the second path 16, and the stopper wall 161 is formed on one end of the second path 16 and is adjacent to the reaction compartment outlet 112. In one embodiment, the extraction module 1 further includes a third path 151 and a fourth path 152. The third path 151 connects the first path 15 to the first waste-liquid compartment 13. The fourth path 152 connects the first path 15 to the second waste-liquid compartment 14. In one embodiment, the first waste-liquid compartment 13 includes a first waste-liquid compartment connection hole 131. The second waste-liquid compartment 14 includes a second waste-liquid compartment connection hole 141. The third path 151 connects the first path 15 to the first waste-liquid compartment connection hole 131. The fourth path 152 connects the first path 15 to the second waste-liquid compartment connection hole 141. At least one portion of the second waste-liquid compartment 14 is located between the first waste-liquid compartment connection hole 131 and the second waste-liquid compartment connection hole 141. In one embodiment, at least one portion of the fourth path 152 extends in a first direction Z, and the first direction Z is away from the first waste-liquid compartment 13. The disclosure is not meant to restrict the present invention.

With reference to FIG. 2, in one embodiment, the second waste-liquid compartment 14 includes a second waste-liquid compartment pressure hole 142. At least one portion of the waste-liquid compartment 14 is located between the first waste-liquid compartment 13 and the second waste-liquid compartment pressure hole 142. In one embodiment, at least one portion of the second path 16 extends in the first direction Z. The disclosure is not meant to restrict the present invention. In one embodiment, the collection compartment 12 includes a collection compartment pressure hole 121. At least one portion of the collection compartment 12 is located between the first waste-liquid compartment 13 and the collection compartment pressure hole 121.

With reference to FIG. 2, in one embodiment, the extraction module 1 further includes an absorbing material 17. The absorbing material 17 is disposed in the first waste-liquid compartment 13. The first waste-liquid compartment 13 includes a first waste-liquid compartment pressure hole 132. At least one portion of the absorbing material 17 is located in a space of the first waste-liquid compartment 13 between the first waste-liquid compartment pressure hole 132 and the first waste-liquid compartment connection hole 131. In one embodiment, the absorbing material 17 can be sponge. In one embodiment, the first waste-liquid compartment pressure hole 132, the second waste-liquid compartment pressure hole 142 and the collection compartment pressure hole 121 are on the same plane.

Figure 3A:
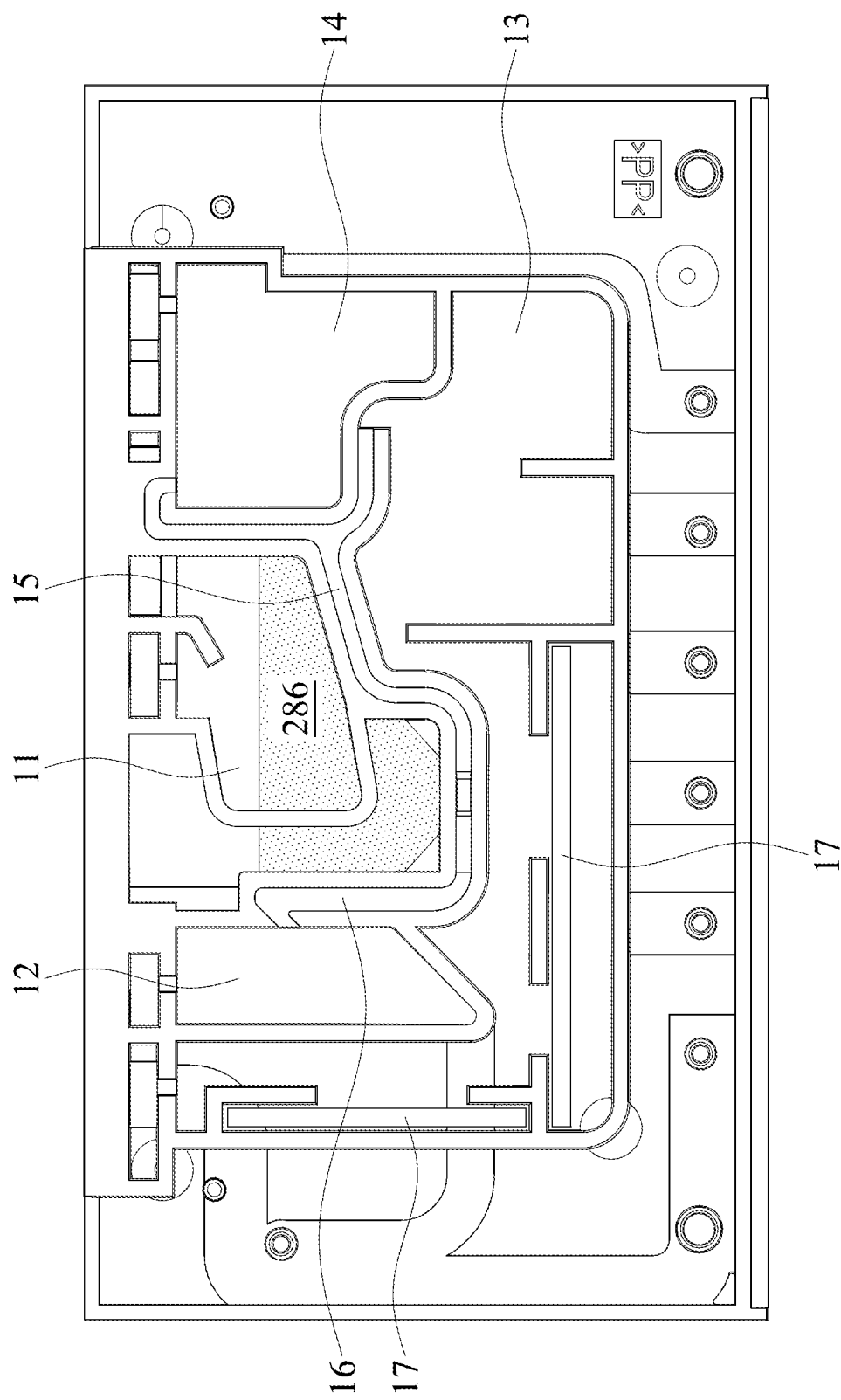
FIGS. 3A, 3B, 3C, 3D, 3E, 3F, 3G, 3H, 3I and 3J show the operation of the extraction module of the embodiment of the present invention.
Figure 3B:
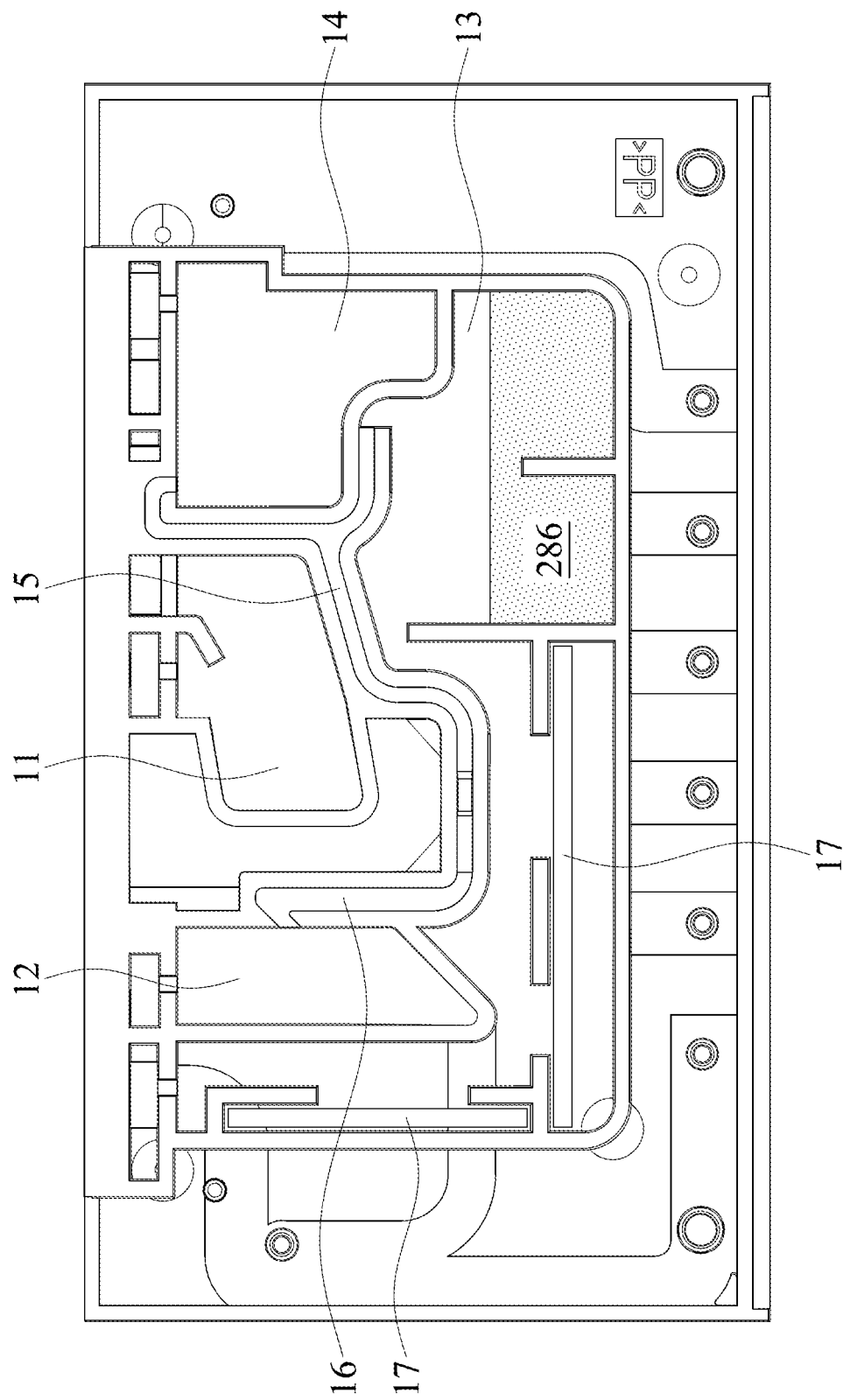
Figure 3C:
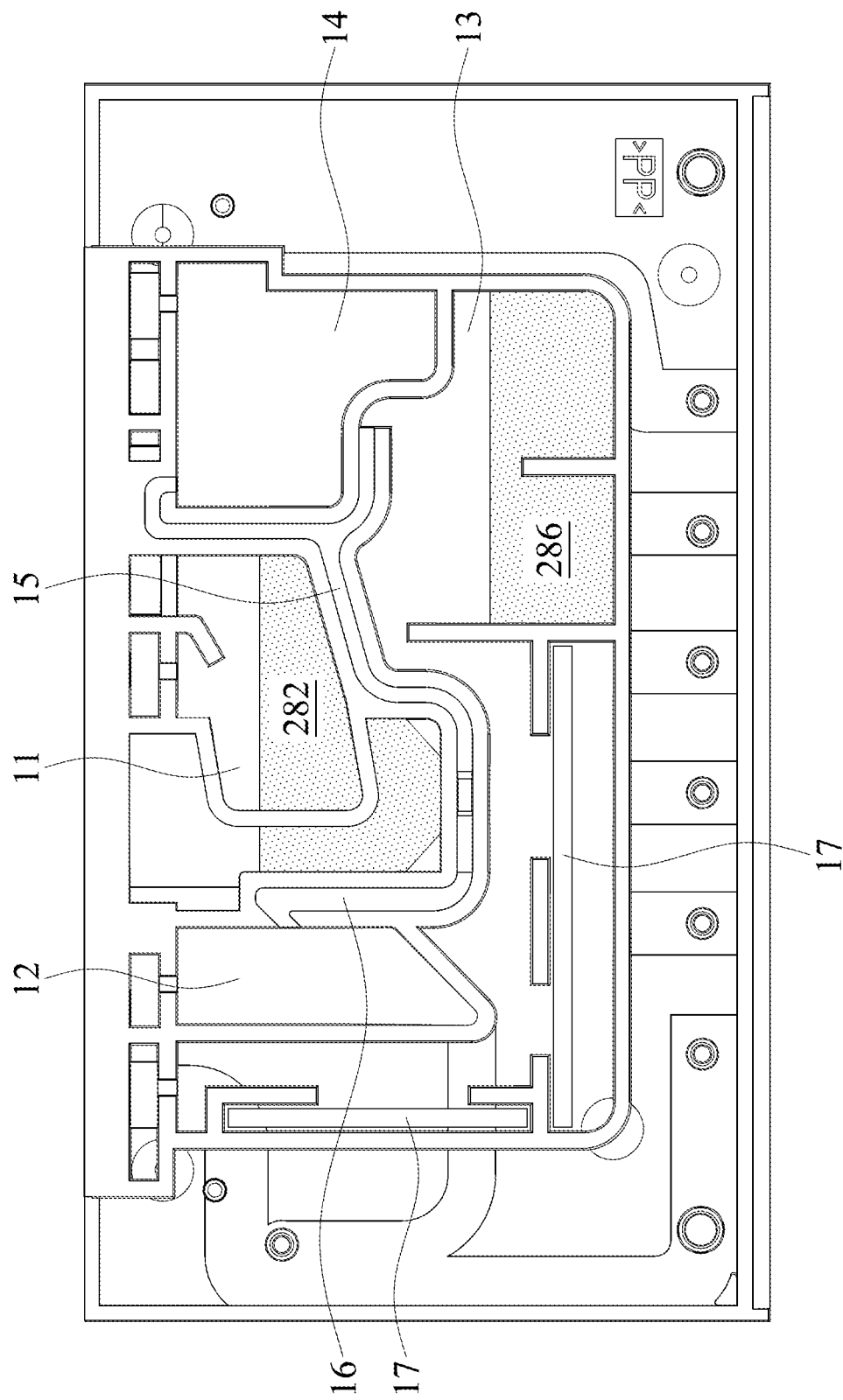

FIGS. 3A-3J show the operation of the extraction module 1 of the embodiment of the present invention. With reference to FIG. 3A, a mixed liquid 286 of sample and alcohol is moved from the liquid receiving module 2 to the expansion compartment 18 and the reaction compartment 11 via the expansion compartment inlet 181, and the filter 111 captures the nucleic acid from the mixed liquid 286. Then, with reference to FIG. 3B, the mixed liquid 286 is moved to the first waste-liquid compartment 13 by a negative pressure (<−10 kpa) provided via the first waste-liquid compartment pressure hole 132. Next, with reference to FIG. 3C, a first detergent 282 is progressively moved from the liquid receiving module 2 to the filter 111 via the expansion compartment inlet 181, expansion compartment 18 and the reaction compartment 11, and the salts concentration and the PH value on the filter 111 is adjusted. Then, with reference to FIG. 3D, the first detergent 282 is moved to the first waste-liquid compartment 13 by the negative pressure (<−10 kpa) provided via the first waste-liquid compartment pressure hole 132. Then, with reference to FIG. 3E, a portion of second detergent 283 is moved from the liquid receiving module 2 to the filter 111 via the expansion compartment inlet 181, expansion compartment 18 and the reaction compartment 11, and the salts concentration and the PH value on the filter 111 is adjusted. Next, with reference to FIG. 3F, the second detergent 283 is moved to the first waste-liquid compartment 13 by the negative pressure (<−10 kpa) provided via the first waste-liquid compartment pressure hole 132. Then, with reference to FIG. 3G, the other portion of second detergent 283 is moved from the liquid receiving module 2 to the filter 111 via the expansion compartment inlet 181, expansion compartment 18 and the reaction compartment 11, and the salts concentration and the PH value on the filter 111 is adjusted. Next, with reference to FIG. 3H, the second detergent 283 is moved to the second waste-liquid compartment 14 by the negative pressure (<−10 kpa) provided via the second waste-liquid compartment pressure hole 142. Then, with reference to FIG. 3I, an eluent 284 is moved from the liquid receiving module 2 to the reaction compartment 11 via the reaction compartment inlet 114, wherein the eluent 284 is resting in the reaction compartment 11 for three minutes, and the nucleic acid is released from the filter 111 to the eluent 284. Next, with reference to FIG. 3J, a big positive pressure (45 kpa) is provided to move the eluent 284 with the nucleic acid is moved to the collection compartment 12. With reference to FIG. 2, in the step of FIG. 3J, a little positive pressure is provided via the second waste-liquid compartment pressure hole 142 to prevent the eluent 284 with the nucleic acid from entering the first path 15. In this embodiment, the big positive pressure (45 kpa) is provided via the liquid receiving module 2 through the reaction compartment inlet 114.

Figure 3D:
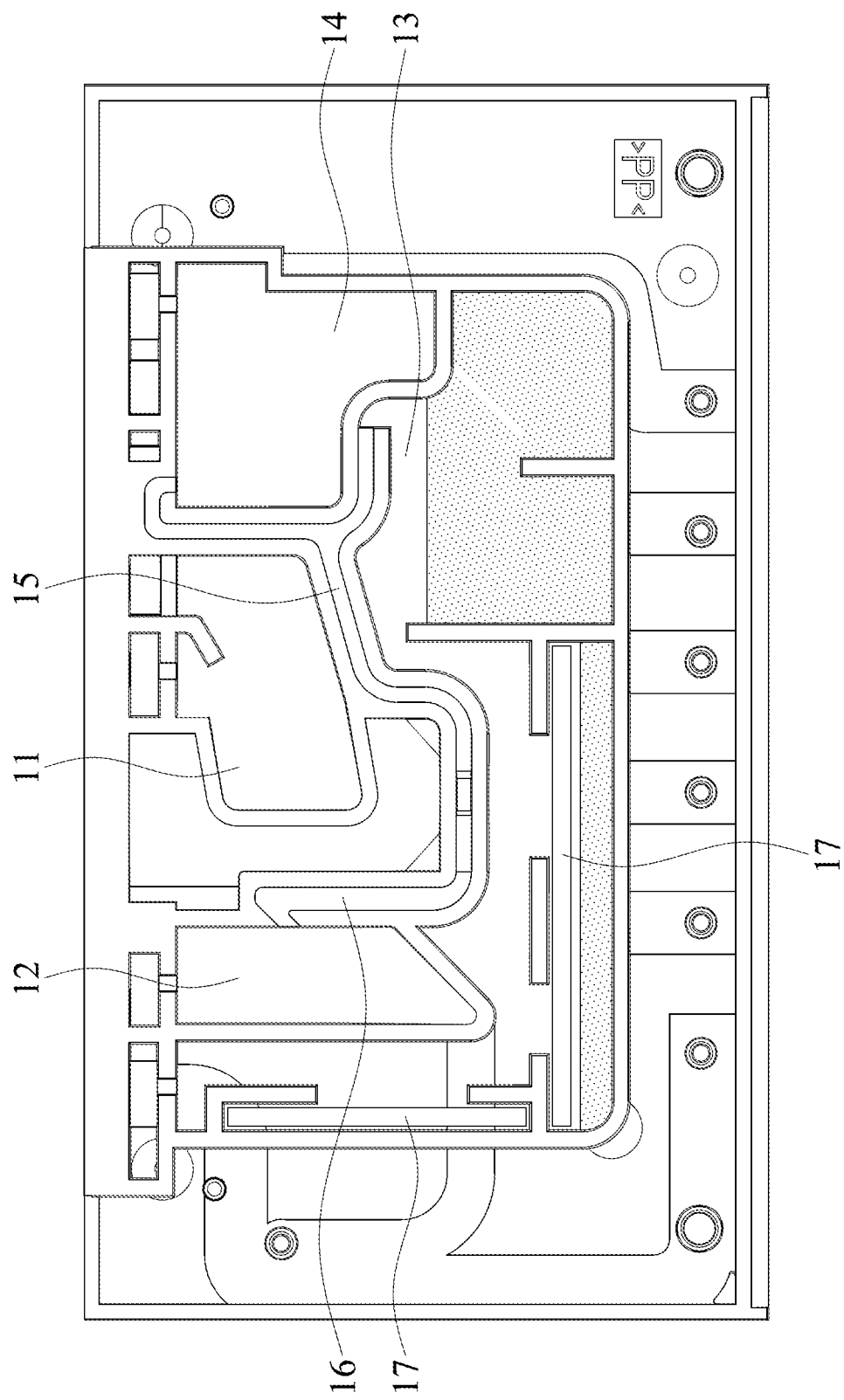
Figure 3E:
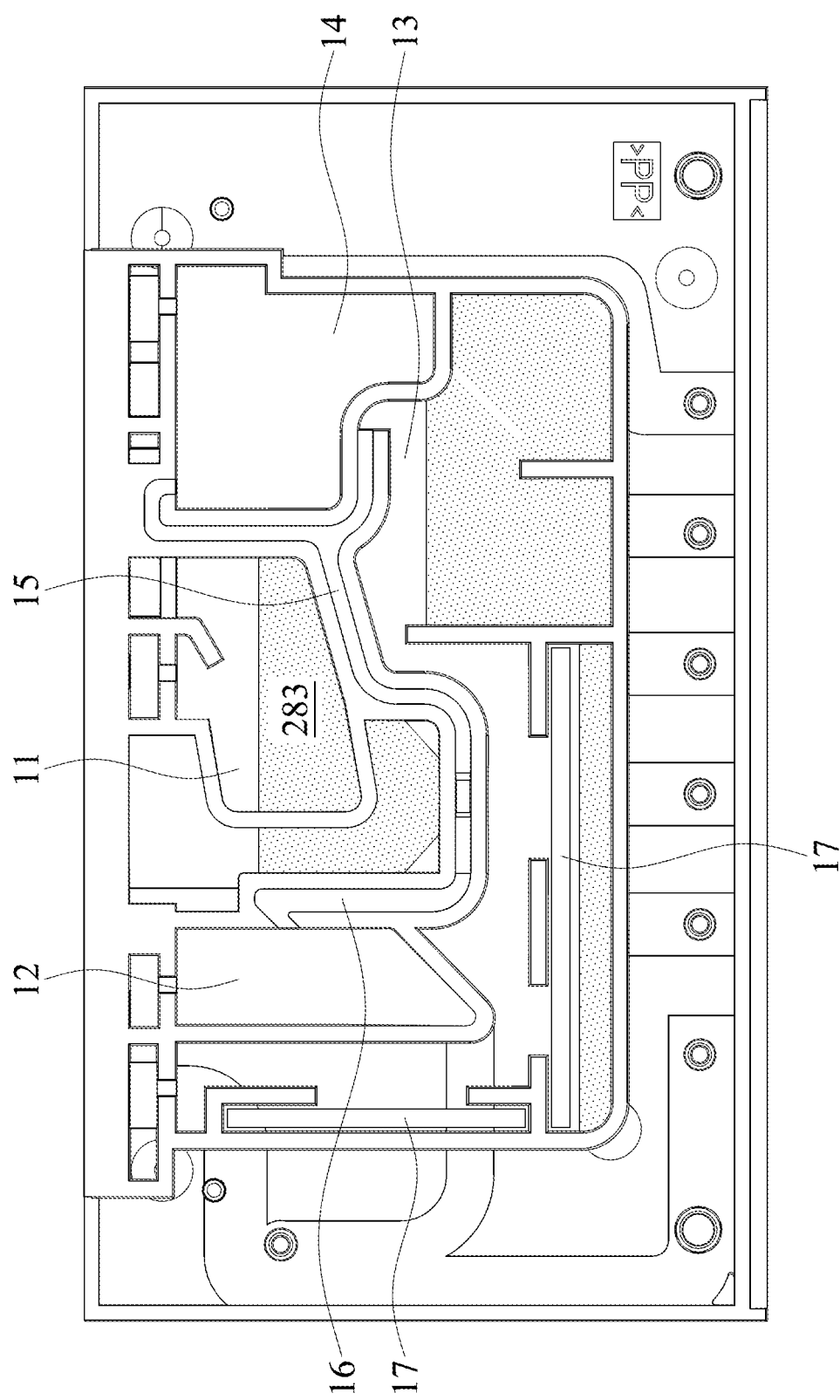
Figure 3F:
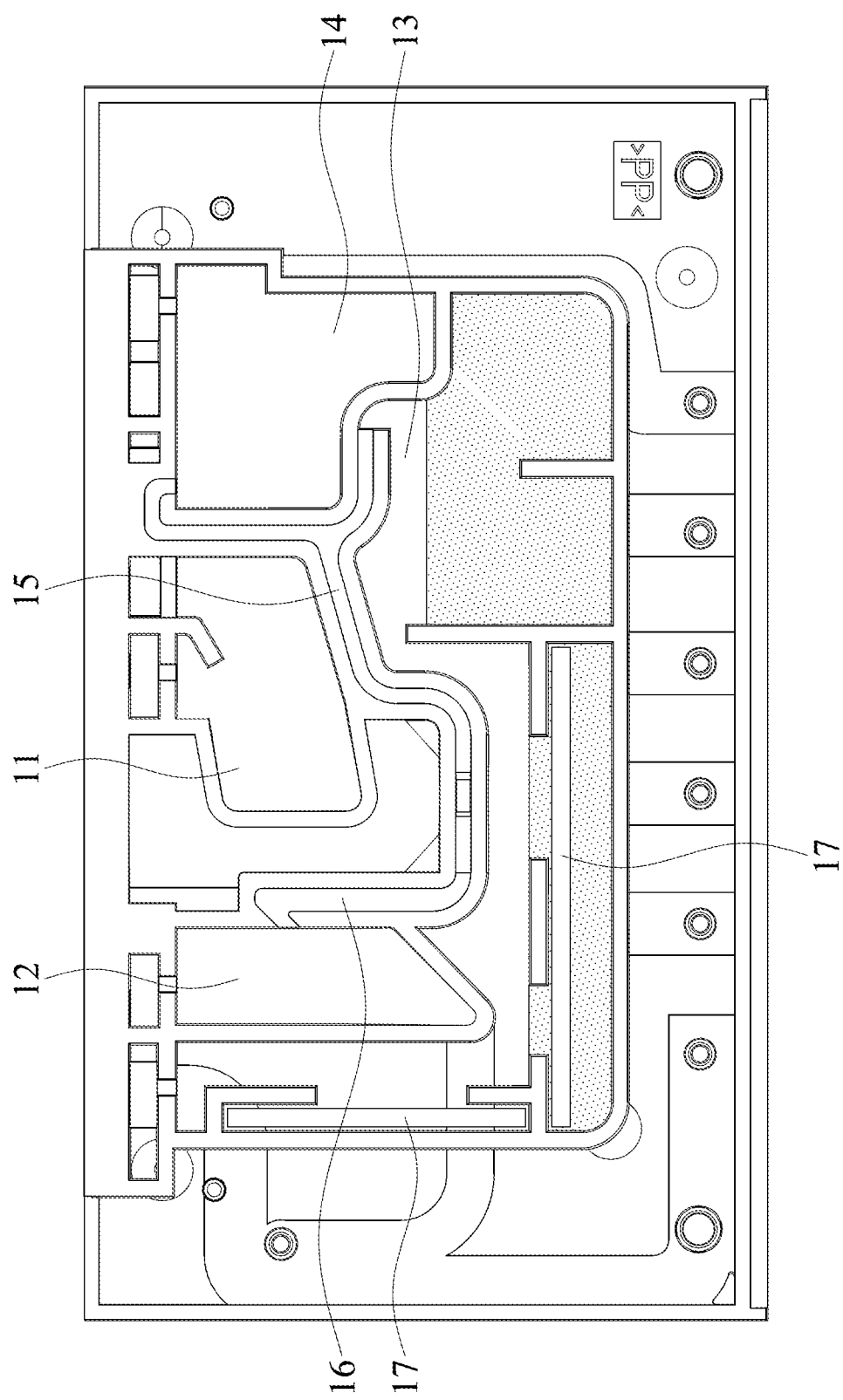
Figure 3G:
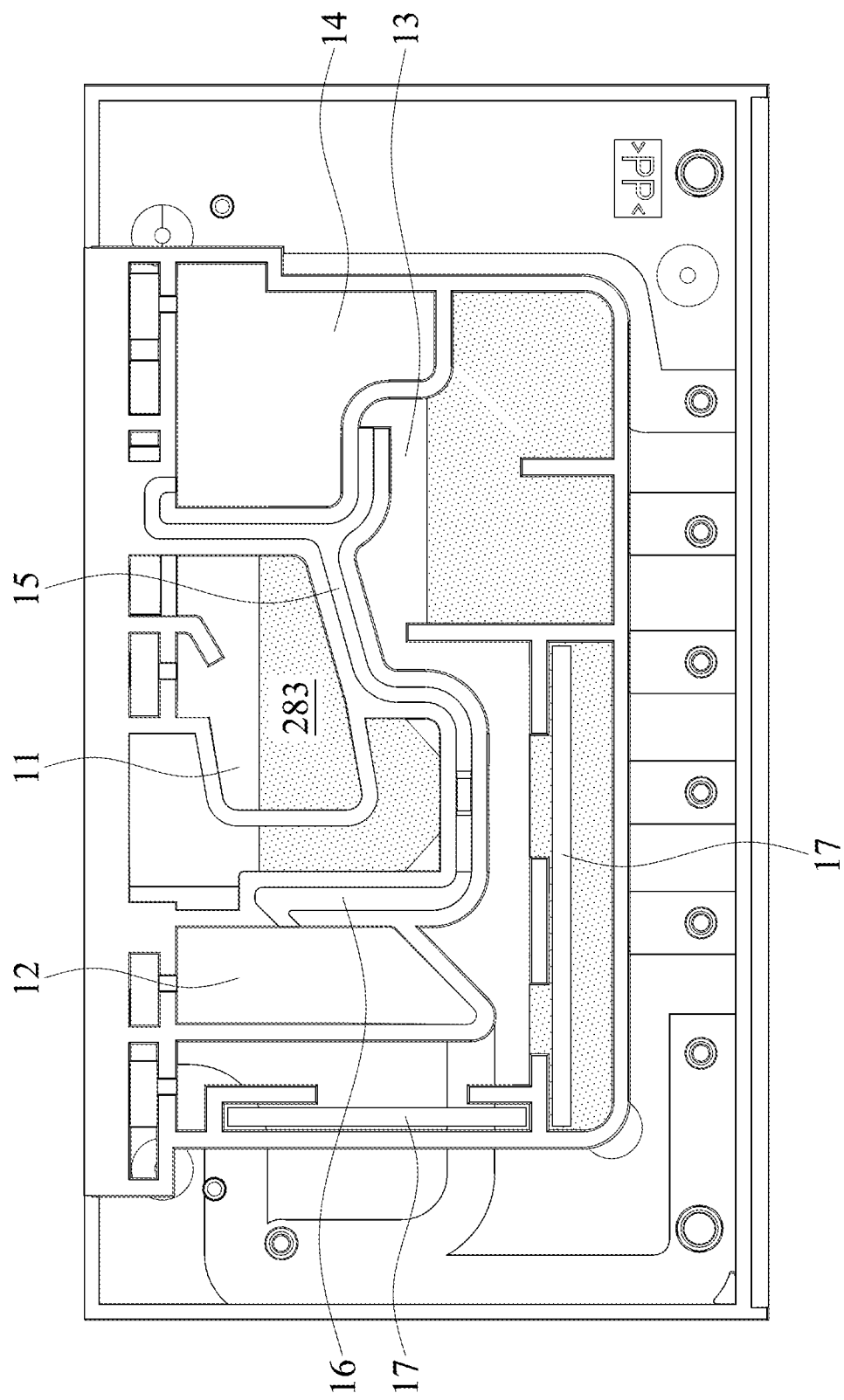

In the steps of FIGS. 3D and 3F, the first detergent 282 can be progressively moved from the liquid receiving module 2 to the filter 111, or totally moved from the liquid receiving module 2 to the filter 111 in single one movement, so does the second detergent 283. The disclosure is not meant to restrict the present invention. In one embodiment, the first detergent 282 can neutralize PH value, and the second detergent 283 can remove protein and organic impurities.

In the embodiments above, the expansion compartment 18 prevents the mixed liquid 286, the first detergent 282 and the second detergent 283 from contacting the reaction compartment inlet 114 to prevent the reaction compartment inlet 114 from being polluted.

With reference to FIG. 2, in the embodiment above, the stopper wall 161 prevents the mixed liquid 286, the first detergent 282 and the second detergent 283 from entering the collection compartment 12. In one embodiment, the second path 16 has a bent portion 162. The bent portion 162 makes the eluent 284 with the nucleic acid to sufficiently enter the collection compartment 12. In one embodiment, the collection compartment 12 further includes a collection compartment inclined surface 122 and a collection compartment outlet 123. The collection compartment inclined surface 122 connects the collection compartment outlet 123. The collection compartment inclined surface 122 makes the eluent 284 with the nucleic acid to totally leave the collection compartment 12 via the collection compartment outlet 123 (to the sampling module 3, with reference to FIG. 1B). In one embodiment, the bent portion 162 is bent toward the collection compartment inclined surface 122.

Figure 3H:
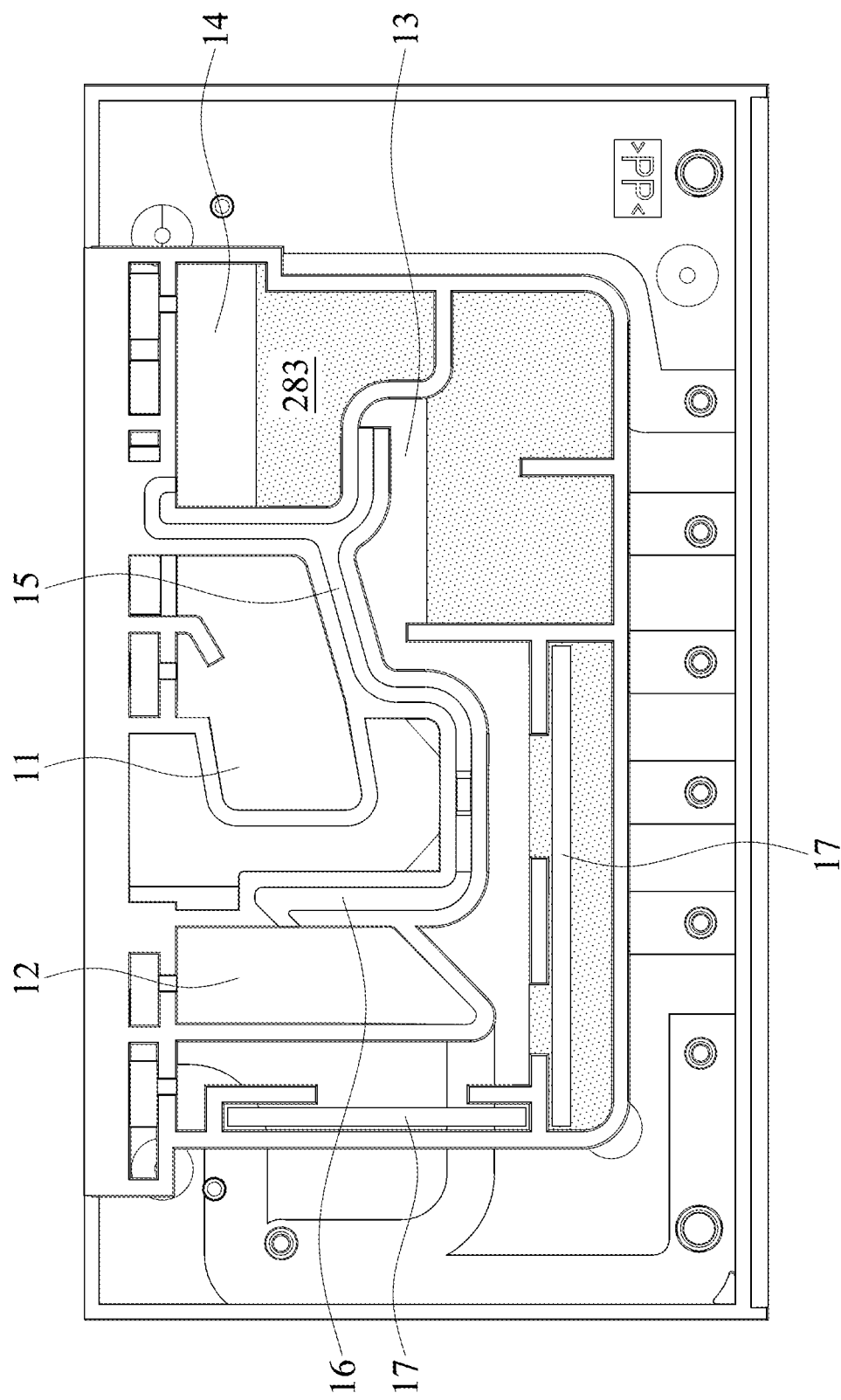
Figure 3I:
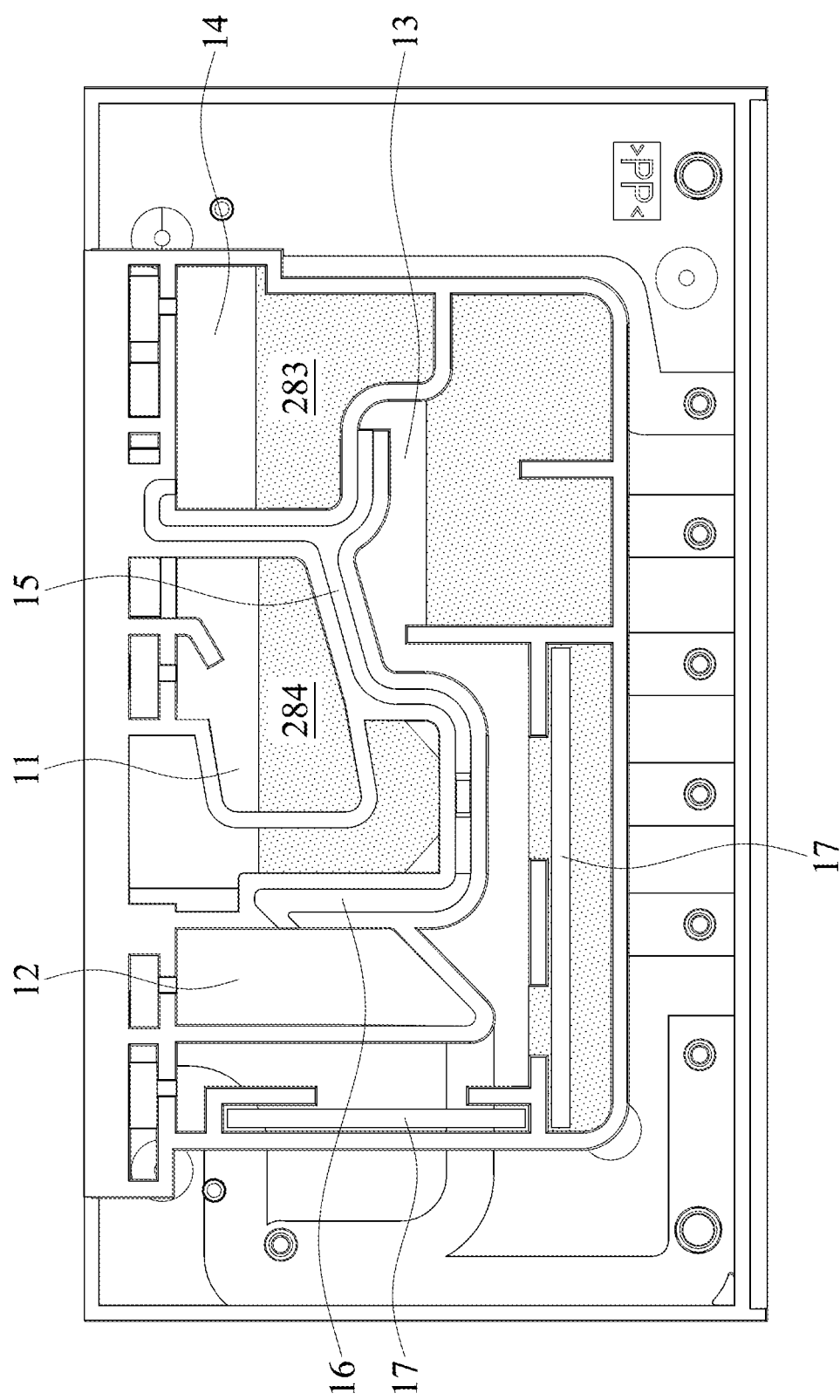
Figure 3J:
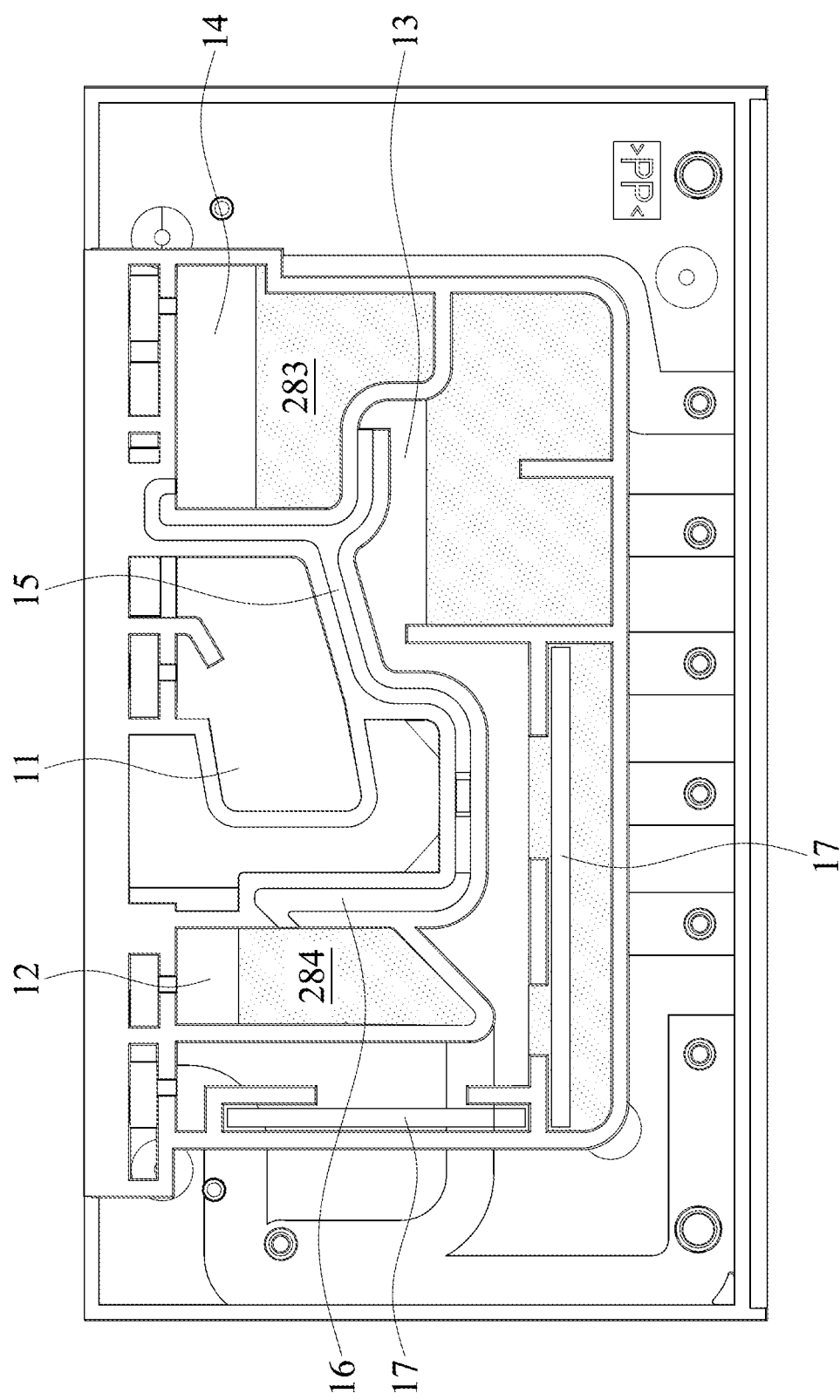

With reference to FIGS. 2 and 3H, the second detergent 283 finally entering the second waste-liquid compartment 14 is the cleanest waste-liquid. In the step of FIG. 3J, the little positive pressure is provided via the second waste-liquid compartment pressure hole 142 to prevent the eluent 284 with the nucleic acid from entering the first path 15. Because the second detergent 283 in the second waste-liquid compartment 14 is the cleanest waste-liquid, the pollution caused by the air inside the second waste-liquid compartment 14 to the eluent 284 can be reduced.

With reference to FIG. 2, in the step of FIG. 3F, the waste-liquid in the first waste-liquid compartment 13 contacts the absorbing material 17. The absorbing material 17 removes the bubbles of the waste-liquid, and the waste-liquid is prevented from overflowing out of the first waste-liquid compartment pressure hole 132. In one embodiment, the filter 111 can be silicon filter or other filters. In one embodiment, the extraction module can be integrally formed.

Figure 4A:
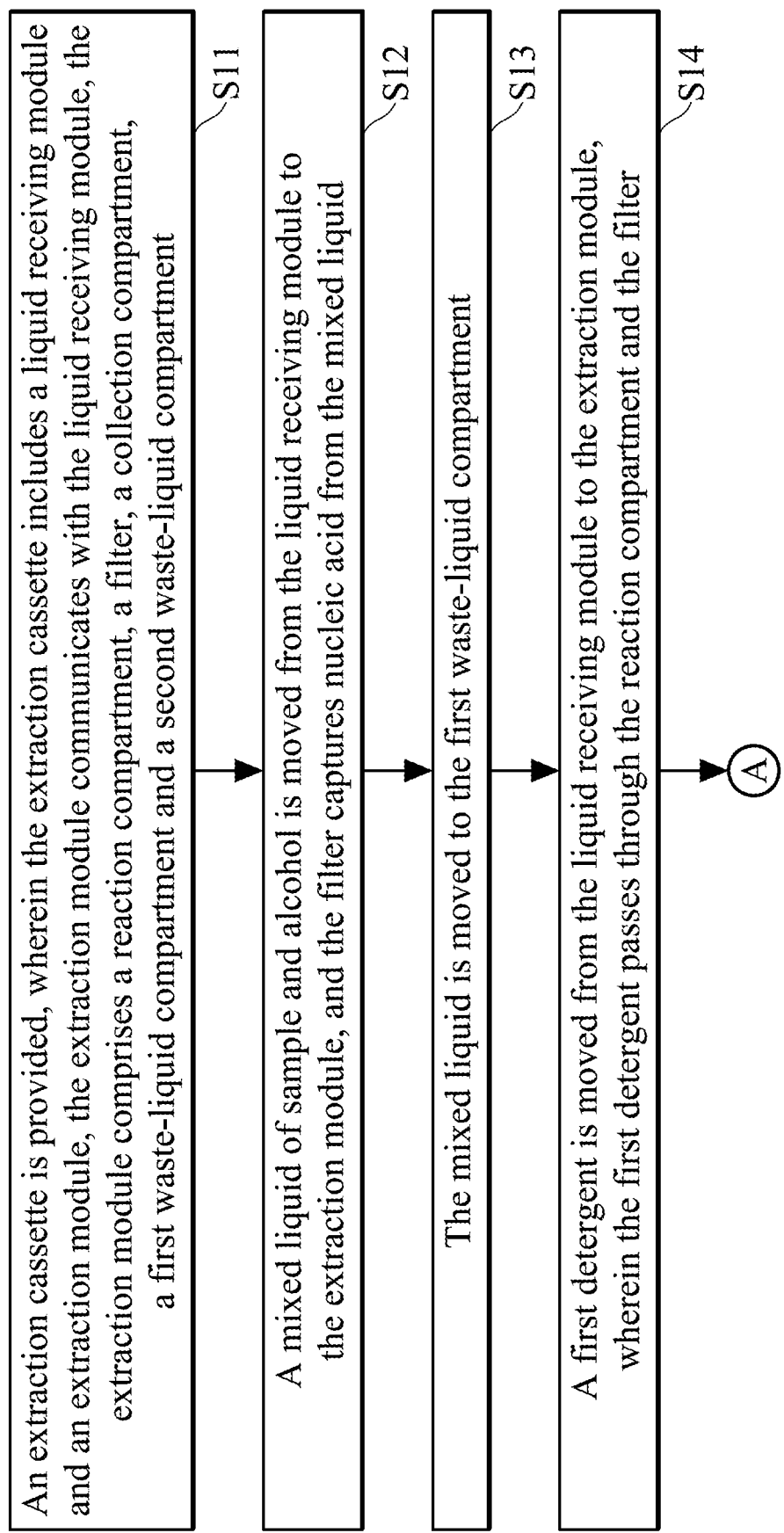
FIGS. 4A and 4B show a method for extracting nucleic acid of the embodiment of the present invention.
Figure 4B:
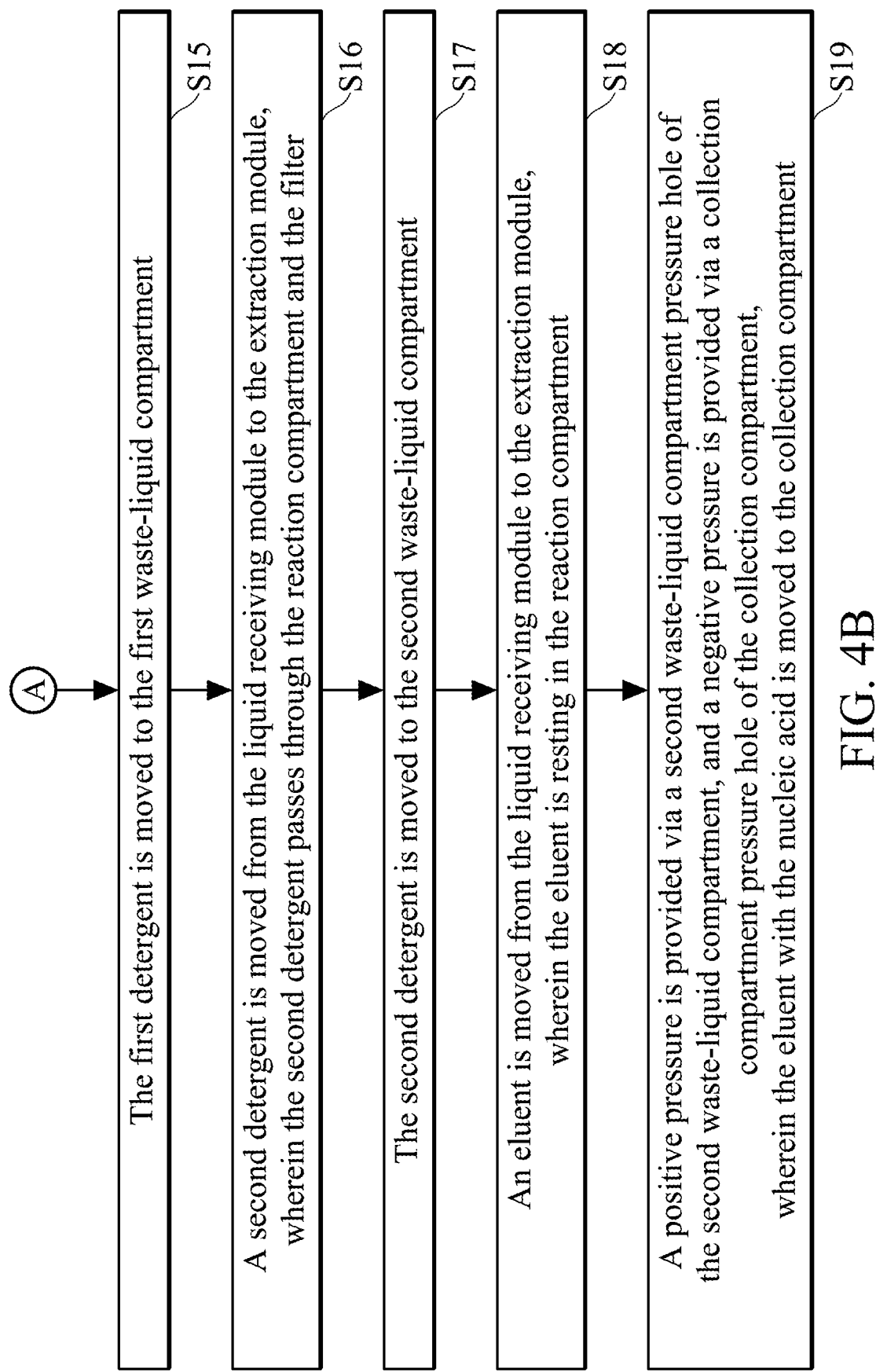

With reference to FIGS. 4A and 4B, in one embodiment, a method for extracting nucleic acid is provided. The method for extracting nucleic acid includes the following steps. First, an extraction cassette is provided, wherein the extraction cassette includes a liquid receiving module and an extraction module, the extraction module communicates with the liquid receiving module, the extraction module includes a reaction compartment, a filter, a collection compartment, a first waste-liquid compartment and a second waste-liquid compartment (S11). Next, a mixed liquid of sample and alcohol is moved from the liquid receiving module to the extraction module, and the filter captures nucleic acid from the mixed liquid (S12). Then, the mixed liquid is moved to the first waste-liquid compartment (S13). Next, a first detergent is moved from the liquid receiving module to the extraction module, wherein the first detergent passes through the reaction compartment and the filter (S14). Then, the first detergent is moved to the first waste-liquid compartment (S15). Next, a second detergent is moved from the liquid receiving module to the extraction module, wherein the second detergent passes through the reaction compartment and the filter (S16). Then, the second detergent is moved to the second waste-liquid compartment (S17). Next, an eluent is moved from the liquid receiving module to the extraction module, wherein the eluent is resting in the reaction compartment (S18). Then, a positive pressure is provided via a second waste-liquid compartment pressure hole of the second waste-liquid compartment, and a negative pressure is provided via a collection compartment pressure hole of the collection compartment, wherein the eluent with the nucleic acid is moved to the collection compartment (S19).

Utilizing the extraction module of the embodiment of the present invention, the reaction compartment and the waste-liquid compartments are incorporated in one single extraction module, and the size and cost of the extraction cassette are reduced. Particularly, by the design of the paths, the reaction compartment, the collection compartment, the first waste-liquid compartment and the second waste-liquid compartment and by the pressure supply, the waste-liquid can be controlled to be moved to the first waste-liquid compartment and the second waste-liquid compartment, and the eluent with the nucleic acid is controlled to be moved to the collection compartment. The waste-liquid is prevented from polluting the reaction compartment and the collection compartment.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term).

While the present invention has been described by way of example and in terms of the preferred embodiments, it should be understood that the present invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An extraction cassette, comprising:
    a liquid receiving module; and
    an extraction module, which communicates with the liquid receiving module, the extraction module comprising:
        an extraction module body;
        an expansion compartment, formed on the extraction module body;
        a reaction compartment, formed on the extraction module body, wherein the reaction compartment comprises a reaction compartment inlet, a reaction compartment outlet and a reaction compartment notch, the expansion compartment is directly connected to the reaction compartment notch, and the reaction compartment notch is located between the reaction compartment inlet and the reaction compartment outlet;
        a filter, disposed in the reaction compartment and corresponding to the reaction compartment outlet;
        a collection compartment, formed on the extraction module body, wherein the collection compartment communicates with the reaction compartment outlet;
        a first waste-liquid compartment, formed on the extraction module body, wherein the first waste-liquid compartment communicates with the reaction compartment outlet; and
        a second waste-liquid compartment, formed on the extraction module body, wherein the second waste-liquid compartment communicates with the reaction compartment outlet,
    wherein the extraction module further comprises a first path and a second path, the first path connects the reaction compartment outlet to the first waste-liquid compartment and the second waste-liquid compartment, and the second path connects the reaction compartment outlet to the collection compartment, wherein the extraction module further comprises a third path and a fourth path, the third path connects the first path to the first waste-liquid compartment, and the fourth path connects the first path to the second waste-liquid compartment, wherein the first waste-liquid compartment comprises a first waste-liquid compartment connection hole, the second waste-liquid compartment comprises a second waste-liquid compartment connection hole, the third path connects the first path to the first waste-liquid compartment connection hole, the fourth path connects the first path to the second waste-liquid compartment connection hole, and at least one portion of the second waste-liquid compartment is located between the first waste-liquid compartment connection hole and the second waste-liquid compartment connection hole.

2. The extraction cassette as claimed in claim 1, wherein the reaction compartment comprises a cone-shaped portion, the filter is disposed on the cone-shaped portion, and the reaction compartment outlet is formed on one end of the cone-shaped portion.

3. The extraction cassette as claimed in claim 1, wherein the first path intersects the second path at the reaction compartment outlet, a stopper wall is formed in the second path, and the stopper wall is formed on one end of the second path and is adjacent to the reaction compartment outlet.

4. The extraction cassette as claimed in claim 1, wherein at least one portion of the fourth path extends in a first direction, and the first direction is away from the first waste-liquid compartment.

5. The extraction cassette as claimed in claim 1, wherein the second waste-liquid compartment comprises a second waste-liquid compartment pressure hole, and at least one portion of the second waste-liquid compartment is located between the first waste-liquid compartment and the second waste-liquid compartment pressure hole.

6. The extraction cassette as claimed in claim 5, wherein at least one portion of the second path extends in a first direction.

7. The extraction cassette as claimed in claim 5, wherein the collection compartment comprises a collection compartment pressure hole, and at least one portion of the collection compartment is located between the first waste-liquid compartment and the collection compartment pressure hole.

8. The extraction cassette as claimed in claim 7, wherein the extraction module further comprises an absorbing material, the absorbing material is disposed in the first waste-liquid compartment, the first waste-liquid compartment comprises a first waste-liquid compartment pressure hole, and at least one portion of the absorbing material is located in a space of the first waste-liquid compartment between the first waste-liquid compartment pressure hole and the first waste-liquid compartment connection hole.

9. The extraction cassette as claimed in claim 8, wherein the first waste-liquid compartment pressure hole, the second waste-liquid compartment pressure hole and the collection compartment pressure hole are on a same plane.

10. The extraction cassette as claimed in claim 1, wherein the expansion compartment further comprises an expansion compartment inlet, an expansion compartment pressure hole and an expansion compartment spacer, the expansion compartment spacer is located between the expansion compartment inlet and the expansion compartment pressure hole, and the expansion compartment spacer is bent toward the expansion compartment pressure hole.

11. A method for extracting nucleic acid, comprising steps of:

providing an extraction cassette, wherein the extraction cassette comprises a liquid receiving module and an extraction module, the extraction module communicates with the liquid receiving module, the extraction module comprises a reaction compartment, an expansion compartment, a filter, a collection compartment, a first waste-liquid compartment and a second waste-liquid compartment, wherein the reaction compartment comprises a reaction compartment inlet, a reaction compartment outlet and a reaction compartment notch, the expansion compartment is directly connected to the reaction compartment notch;

moving a mixed liquid of sample and alcohol from the liquid receiving module to the extraction module, and the filter captures nucleic acid from the mixed liquid;

moving the mixed liquid to the first waste-liquid compartment;

moving a first detergent from the liquid receiving module to the extraction module, wherein the first detergent passes through the reaction compartment and the filter; and moving the first detergent to the first waste-liquid compartment.

12. The method as claimed in claim 11, further comprising steps of:

moving a second detergent from the liquid receiving module to the extraction module, wherein the second detergent passes through the reaction compartment and the filter;

moving the second detergent to the second waste-liquid compartment;

moving an eluent from the liquid receiving module to the extraction module, wherein the eluent is resting in the reaction compartment; and providing a positive pressure via a second waste-liquid compartment pressure hole of the second waste-liquid compartment, and providing a negative pressure via a collection compartment pressure hole of the collection compartment, wherein the eluent with the nucleic acid is moved to the collection compartment.

\* \* \* \* \*